United States Patent [19]

America

[11] Patent Number: 4,587,014
[45] Date of Patent: May 6, 1986

[54] LIQUID CHROMATOGRAPHY COLUMN ASSEMBLY

[75] Inventor: William G. America, Danbury, Conn.

[73] Assignee: The Perkin-Elmer Corporation, Norwalk, Conn.

[21] Appl. No.: 607,878

[22] Filed: May 7, 1984

[51] Int. Cl.[4] .............................................. B01D 15/08
[52] U.S. Cl. .................... 210/198.2; 55/386
[58] Field of Search ....................... 210/198.2; 55/386

[56] References Cited

U.S. PATENT DOCUMENTS

| | | | |
|---|---|---|---|
| 3,904,527 | 9/1975 | Wilhelmson et al. | 210/198.2 |
| 3,981,801 | 9/1976 | Knox | 210/198.2 |
| 4,026,803 | 5/1977 | Abrahams et al. | 210/198.2 |
| 4,280,905 | 7/1981 | Gunkel et al. | 210/198.2 |
| 4,283,280 | 8/1981 | Brownlee | 210/198.2 |
| 4,288,322 | 9/1981 | Guillemin et al. | 210/198.2 |
| 4,476,017 | 10/1984 | Scharff | 210/198.2 |

OTHER PUBLICATIONS

Chrompack General Catalog, 1981, pp. 55 and 70, Chrompack Inc., Bridgewater, N.J.

Primary Examiner—John Adee
Attorney, Agent, or Firm—E. T. Grimes; F. L. Masselle

[57] ABSTRACT

A liquid chromatography column assembly includes a separation column having stationary phase retaining frits is positioned within a housing adapted to accept conventional column termination fittings. The assembly includes a sealed cylindrical cavity to ensure radial distribution of the incoming fluid across the cross-section of the column.

1 Claim, 2 Drawing Figures

LIQUID CHROMATOGRAPHY COLUMN ASSEMBLY

BACKGROUND OF THE INVENTION

The present invention generally relates to a liquid chromatography column assembly and, in particular, relates to such an assembly having means for establishing a sealed cylindrical cavity at one end thereof.

Most conventional liquid chromatography columns, during manufacture, are provided with end fittings which, in general, act to ensure the retention of the packing material. Usually, the packing material completely fills the column and is retained by the end fittings each of which includes a frit element. The frit element serves both as a seal against the loss of packing material and as a radial distribution element to distribute the incoming fluid substantially evenly across the cross-section of the column. In some commercial columns the frit is initially press-fit into the fitting before the fitting is placed on the column.

As a consequence of these manufacturing techniques the purchase price of a column must necessarily include the cost of the fittings. That is, whenever the useful life of a column expires a new set of fittings must also be purchased.

In recent years, throw-away cartridge columns have been introduced which do not require new fittings each time a column is replaced.

To date, however, such cartridge columns have exhibited a number of drawbacks. For example, some frit retainer arrangement has been required to properly position the frit and simultaneously retain the efficient radial distribution of fluid across the column.

One such assembly is described in U.S. Pat. No. 3,682,315 issued to Haller on Aug. 8, 1972. The assembly therein requires a self-sealing septum and includes a member extending into the column and to maintain a specific distance between the system and the frit. The member also acts to seal the column against leakage or loss of packing material. Such a member, in one form or another, is common in present cartridge column assemblies. In addition, the sealing of the column is somewhat complex. Thus, understandably, the cost of the column is still relatively high, and the assembly somewhat complex.

SUMMARY OF THE INVENTION

Accordingly, it is one object of the present invention to provide a liquid chromatography column assembly which is simple to manufacture and use as well as being chromatographically efficient and inexpensive.

This object is achieved, at least in part, by a cartridge assembly having a means for establishing a sealed cylindrical cavity between the fluid entry and the column.

Other objects and advantages will become apparent to those skilled in the art from the following detailed description read in conjunction with the appended claims and drawings attached hereto.

BRIEF DESCRIPTION OF THE DRAWING

The drawing, not drawn to scale, includes.

DETAILED DESCRIPTION OF THE INVENTION

Figure 1:
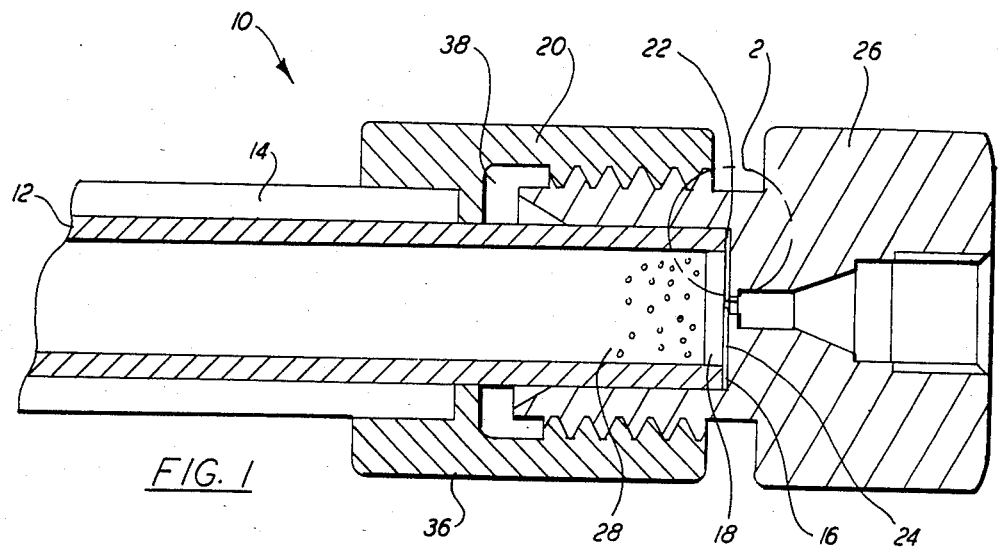
FIG. 1 which is a cross-sectional view of a cartridge column assembly embodying the principles of the present invention.

A liquid chromatography column assembly, generally indicated at 10 in the drawings and embodying the principles of the present invention, includes a liquid chromatography column 12 positioned within a tubular housing 14. The column 12 includes, proximate at least one end 16 thereof, a frit 18 which frit 18 being slightly recessed from the one end 16. The assembly 10 also includes a fitting retention member 20 which member 20 is securely affixed to the tubular housing 14. The assembly 10 further includes a means 22 for establishing a sealed cylindrical cavity 24 at the one end 16 of the column 12. The assembly 10 attaches to a conventional column termination fitting 26 via the member 20 and thus secured to the one end 16.

For convenience and consistency of operation the column assembly 10 is symmetrical, i.e., the ends of the column 12 and housing 14 are identical. However, only one end arrangement is shown in the drawings and discussed in detail herinafter.

Figure 2:
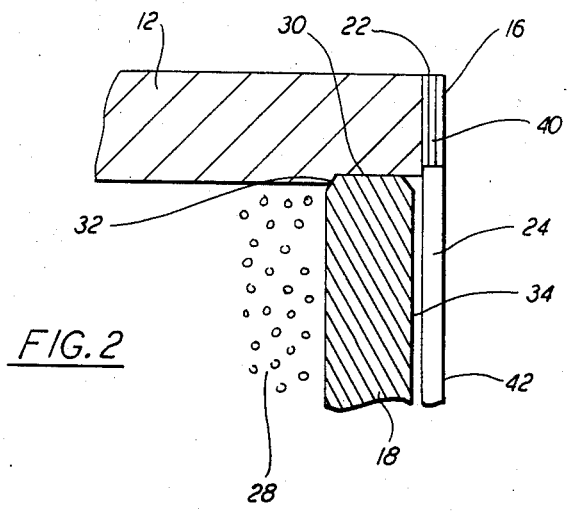
FIG. 2 which is a detailed view of a portion of one end of the assembly.

In a preferred embodiment, the liquid chromatography column 12 is a stainless steel tube packed with a preselected chromatographic stationary phase material 28. The column 12 includes a segment 30, shown in FIG. 2, having an enlarged diameter proximate the end 16 which segment 30 forms a recessed shoulder 32 at the interior terminus thereof. The material 28 within the column 12 is retained by the frit 18 which is press fitted into the segment 30 against the shoulder 32. The thickness of the frit 18 and the depth of the segment 30 are chosen to ensure that the surface 34 of the frit 18 proximate the end 16 is recessed within the segment 30. The column 12, including the retaining frits 18, is positioned within the housing 14.

Preferably, the housing 14 includes a stainless steel tube having an inside diameter slightly larger than the outside diameter of the column 12. Thus, the column 12 slides freely into the housing 14. The housing 14, as discussed above, includes a fitting retention member 20 at the end thereof. The fitting retention member 20 is, preferably, rigidly affixed to the housing 14 and includes a portion 36 which extends beyond the tubular housing 14. The portion 36 is provided with an internally threaded opening 38 designed to accept a conventionally externally threaded column terminator fitting 26.

The means 22 for establishing the sealed cylindrical cavity 24 preferably includes a thin semi-rigid gasket 40 having an opening 42 therethrough which opening 42 has a diameter at least equal to that of the inside diameter of the column 12. As an alternative, the gasket 40 can be sized so that the opening 42 therethrough has a diameter at least equal to that of the segment 30.

In one specific embodiment, the tubular housing 14 is 8 cm long and has an inside diameter of about 7 millimeter. The fitting retention member 20 is welded or brazed to the housing 14 and extends about 1 centimeter from the end thereof. The member 20 is, for example, the female part of a quarter-inch tube nut fitting having a 7/16–20 internal thread. The column 12, useful in such a housing 14 is about 8.5 cm long and has an outside diameter of about 6.3 millimeter. The frit has conventionally a porosity of 0.5 micrometers and is about 0.8 millimeters thick. The frit 18 has an outside diameter of about 4.8 millimeters. The corresponding enlarged segment 30 of the column 14 has an inside diameter of 4.7 millimeters producing a shoulder 32 which is about 0.05 millimeters. The shoulder 32 is about 7.8 millimeters from the one end 16 of the column 12. Hence, when assembled, a cavity volume of between 1.4 microleters and 2.2 microleters is formed between the frit 18 and the end 16 of the column. The gasket 40 has an outside diameter equal to that of the column 12 and an inside diameter which is at least equal to the diameter of the enlarged segment 30. Preferably, the gasket 40 is formed from Kapton, a material manufactured and marketed by DuPont Corp. of Wilmington, Del. The initial thickness of the gasket 40 is chosen to be about 0.14 millimeters.

In practice, a customer would need to purchase only a single housing 14 for each particular column length to be used. Thereafter, only a replacement column 12 having frits 18 press fitted into the enlarged segment 30 thereof and gaskets 40 would need to be purchased.

Thus, to employ the present assembly 10, the chromotographer inserts the column 12 into the housing 14 and, after placing the gasket 40 at the ends of the column 12, attaches the conventional fittings 26 to the members 20. In order to ensure that any conventional fitting 26 can be used, the column 12 and the housing 14 are cooperatively sized so that the column 12 extends slightly beyond the members 20. Hence, the formation of the sealed cavity 24 is ensured. Further, upon attachment of the fittings 26 to the gaskets 40 are to compress to a thickness of about 0.09 millimeters. Alternately, the gasket 40 could be first inserted into the conventional end fittings 26 and thereby, upon attachment thereof, for the desired sealed cavity.

The assembly 10 described herein not only is inexpensive and considerably less complex to use but is also chromatographically efficient. The efficiency is maintained by the establishment of the sealed cylindrical cavity 24 which ensures excellent vradial distribution of the entering fluid.

The present assembly has been described herein via an exemplary embodiment. Other arrangements and configurations may be developed by those skilled in the art without departing from the spirit and scope of this description. Hence, the present invention is deemed limited only by the claims appended hereto and the reasonable interpretation thereof.

What is claimed is:

1. A liquid chromatography column assembly comprising, in combination:

a liquid chromatography separation column;

a housing having said column positioned therein;

retaining means affixed to said housing for retaining a column injection fitting; said retaining means including a portion extending beyond said housing, said portion having an internally threaded opening, said column extending beyond said portion of said fitting retaining means;

a semi-rigid gasket disposed between the end of said column and a column injection fitting, said gasket having an inside diameter at least equal to the inside diameter of said column;

a porous frit disposed adjacent the end of said column through which frit liquid must pass prior to entry into said column; and said housing, said frit, said semi-rigid gasket and said retaining means being shaped so that in use a sealed substantially cylindrical cavity is formed between the fitting to which said retaining means couples and said frit thereby permitting substantially uniform injection of liquid into said column through said frit.

* * * * *